United States Patent [19]
Kaminsky et al.

[11] Patent Number: 4,769,510
[45] Date of Patent: Sep. 6, 1988

[54] PROCESS FOR THE PREPARATION OF POLYOLEFINS

[75] Inventors: Walter Kaminsky, Pinneberg; Klaus Külper, Hamburg; Maria Buschermöhle, Hamburg; Hartmut Lüker, Hamburg, all of Fed. Rep. of Germany

[73] Assignee: Hoechst Aktiengesellschaft, Frankfurt am Main, Fed. Rep. of Germany

[21] Appl. No.: 801,683

[22] Filed: Nov. 25, 1985

[30] Foreign Application Priority Data

Nov. 27, 1984 [DE] Fed. Rep. of Germany ....... 3443087

[51] Int. Cl.[4] ........................... C07C 2/30; C07C 2/32
[52] U.S. Cl. .................................. 585/512; 526/160; 526/165; 585/523
[58] Field of Search ................ 526/160, 165; 585/510, 585/512, 523

[56] References Cited

U.S. PATENT DOCUMENTS

| 4,522,982 | 6/1985 | Ewen | 526/160 |
| 4,530,914 | 7/1985 | Ewen et al. | 526/160 |
| 4,542,199 | 9/1985 | Kaminsky et al. | 526/160 |

Primary Examiner—Asok Pal

[57] ABSTRACT

In the polymerization of propylene and other higher 1-olefins, polymers which have a high degree of isotacticity and a narrow distribution of molecular weight are obtained in the presence of a catalyst system composed of a zirconium compound which is stereo-rigid and chiral and a linear or cyclic aluminoxane. In addition, the catalyst system is exceptionally active.

2 Claims, No Drawings

PROCESS FOR THE PREPARATION OF POLYOLEFINS

The present invention relates to a process for the polymerization of propylene and higher 1-olefins and for the copolymerization of propylene with ethylene or higher 1-olefins using new Ziegler catalyst systems. The invention relates, in particular, to a process for the preparation of propylene homopolymers and copolymers in which the polymerization is carried out in the presence of a catalyst system comprising a stereo-rigid, chiral zirconium compound and an aluminum alkyl compound containing oxygen.

Recently, so-called supported catalyst systems have, in particular, been employed in the preparation of polypropylene of high isotacticity. These are mixed catalysts in which the transition metal component is prepared, for example, by bringing into contact with one another a magnesium halide, an electron donor and a titanium compound, and in which aluminum alkyls are employed as an activator. Catalysts of this type are described, for example, in German Offenlegungsschrift No. 2,230,672 and in European Pat. No. 7,061. These catalyst systems possess a high activity and they afford polypropylene which is characterized by a high isotacticity and a broad distribution of molecular weight, $M_w/M_n$, of 7 to 11.

Soluble Zeigler catalysts are also known. Thus, for example, German Offenlegungsschriften Nos. 3,007,725 and 3,127,133 describe processes for the preparation of polyolefins which are carried out using bis-(cyclopentadienyl)-zirconium-alkyl and/or bis-(cyclopentadienyl)-zirconium-halogen compounds in combination with oligomeric aluminoxanes. Although these soluble catalyst systems display a very high activity in the polymerization of ethylene and propylene, in the case of propylene polymerization a product of very low stereo-specificity is obtained, i.e. polypropylene which is quite predominantly atactic is obtained.

It has now been found that polymers which have a high isotacticity and a narrow distribution of molecular weight are obtained when propylene and other higher 1-olefins are polymerized in the presence of a catalyst system composed of (a) a zirconium compound which is stereo-rigid and chiral and corresponds to the general formula $$R^3ZrA^1A^2R^1R^2,$$

and (b) a compound of the aluminoxane type containing aluminum and having the general formulae $$Al_2OR_4(Al(R)-O)_n$$

for a linear aluminoxane and $$(Al(R)-O)_{n+2}$$

for a cyclic aluminoxane, n being 4 to 20 and R being methyl or ethyl.

Additionally, the catalyst systems are exceptionally active. The stereo-rigid, chiral zirconium compound of the catalyst system to be employed in the process according to the invention is a π-linked, unsymmetrical, mononuclear or polynuclear compound which contains linear or cyclic hydrocarbon chains as bridges and corresponds to the following general structural formula:

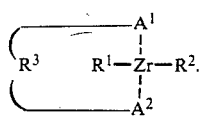

In this formula, $A^1$ and $A^2$ denote a mononuclear or polynuclear, unsymmetrical hydrocarbon radical, it being possible for $A^1$ and $A^2$ to be different but preferably being identical, preferably an indenyl group or a substituted cyclopentadienyl group, in particular 4,5,6,7-tetrahydro-1-indenyl, $R^3$ being a linear $C_1$ to $C_4$ hydrocarbon radical or a cyclic $C_3$ to $C_6$ hydrocarbon radical and $R^1$ and $R^2$ being halogen, preferably Cl, or a $C_1$ to $C_6$ alkyl radical, it being possible for $R^1$ and $R^2$ to be identical or different.

Ethylene-bis-(4,5,6,7-tetrahydro-1-indenyl)-zirconium dichloride is particularly preferred.

The optically active zirconium compounds are employed in the form of a racemate. The pure D-form or L-form can also be used, however.

The organo-aluminum catalyst components used are aluminoxanes of the general formulae $Al_2OR_4(Al(R)-O)_n$ for linear aluminoxane and $(Al(R)-O)_{n+2}$ for cyclic aluminoxane, in which n is an integer from 4 to 20 and R is a methyl or ethyl radical, preferably a methyl radical. The preparation of compounds of this type is known. It is important that the aluminoxanes should have a degree of polymerization of at least 6; preferably it is over 10.

The monomers employed in the preparation of homopolymers are olefins for the formula $CH_2=CHR$ in which R is $C_1$ to $C_{10}$ alkyl. It is preferable to use propylene. In the preparation of copolymers, the said olefins are employed as a mixture or mixed with ethylene. The ratio of the monomers to one another can be varied within wide ranges in the preparation of the copolymers. In particular, it is also possible to copolymerize ethylene in considerable amounts, for example even more than 50%. The properties of the copolymer can be varied within wide ranges by selecting the comonomers and the mixing ratio in a particular case.

The polymerization is carried out in solvent, in the liquid monomers or in the gas phase. It is advantageous if an aluminoxane concentration of $10^{-4}$ to $10^{-1}$ mol per liter, and aluminum and zirconium in an atomic ratio of 10:1 to $10^8$:1 are used in the polymerization in solvents.

The polymerization is carried out at a temperature within the range from 31 50° to 200° C., but preferably at $-20°$ to 120° C.; the range between $-20°$ C. and $+60°$ C. is particularly preferred.

The average molecular weight of the polymers formed can be controlled in a manner known per se by adding hydrogen and/or varying the temperature. Higher molecular weights are achieved at low temperatures; lower molecular weights at higher temperatures.

The polyolefins obtained by the process according to the invention are distinguished by a very high degree of isotacticity. Whereas polypropylenes hitherto known (for the method of determining the isotacticity index cf. F. Kloos and H. G. Leugering, IUPAC Macro Florence Reprints 2, 479 (1980) have a soluble content of at least 2 to 7% by weight, determined by recrystallization in hydrocarbons, polypropylenes can be prepared by the process according to the invention which—when examined by the same method—have a soluble content of substantially less than 1%. Hence 99% by weight or more of the polypropylene obtained by the process according to the invention are crystalline.

The polyolefins prepared in accordance with the invention are further distinguished by an exceedingly narrow molecular weight distribution. Whereas polypropylenes prepared by know processes usually have a molecular weight distribution within the range of Mw/Mn=7 to 11, the polypropylenes prepared by the process according to the invention have a molecular weight distribution Mw/Mn down to approx. 2. This results in a pattern of properties for the polymers which makes them paricularly suitable for injection molding, especially for the production of precision parts and the like.

Additionally, the catalyst systems employed in the process according to the invention are particularly active. The activity of these catalyst systems exceeds, for example, even the caralysts in which cyclopentadienyl-zirconium compounds and aluminoxane are employed and by means of which atactic polypropylene is obtained.

EXAMPLE 1

(a) Preparation of methyl aluminoxane 44.3 g of $Al_2(SO_4)_3.16H_2O$ (0.056 mol, corresponding to 1 mol of $H_2O$) were suspended in 250 ml of toluene, 50 ml of aluminum trimethyl (0.52 mol) were added and the mixture was allowed to react at 20° C. After a reaction time of 30 hours, approx. 0.9 mol of methane had been evolved. The solution was then filtered to free it from solid aluminum sulfate. Removing the toluene gave 19.7 g of methyl aluminoxane. The yield was 63% of theory. The average molecular weight, determined cryoscopically in benzene, was 1,170.

The average degree of oligomerization was approx. 16.

(b) Preparation of ethylene-bis-(4,5,6,7-tetrahydroindenyl)-zirconium dichloride The preparation was carried out in the same manner as that described in the Journal of Organometallic Chemistry, 232, (1982) page 245/246 for ethylene-bis-(4,5,6,7-tetrahydroindenyl)-titanium dichloride.

(c) Polymerization

A 1-liter glass autoclave, purged by heating and flushed several times with argon, was filled, while under thermostatic control at +20° C., with 330 ml of absolute toluene, 360 mg of methyl aluminoxane having an average degree of oligomerization of 16 and 3.3 $\times 10^{-6}$ mol of racemic ethylene-bis-(4,5,6,7-tetrahydroindenyl)-zirconium dichloride. 70 ml of propylene were then condensed rapidly into this solution, the mixture becoming cloudy after a few minutes. After a polymerization time of 2 hours, the pressure had fallen from 3.1 bar to 1.5 bar. The polymerization was then terminated by blowing off the excess monomer while adding ethanol.

Residues of catalyst were removed by stirring with HCl solution, and the polymer was then filtered off with suction and dried to constant weight at 60° C. The yield of white, pulverulent, isotactic polypropylene was 31.3 g; the activity was thus 4,750 kg of PP/mol of Zr.h. at an Mn of 41,000.

The content of atactic polypropylene (APP) was 1.0% (fraction soluble in a high-boiling petroleum ether fraction at 130° C.). GPC determination in 1,2,4-trichlorobenzene/135° C. gave an $M_w/M_n$ value of 1.9.

EXAMPLE 2

The procedure was as in Example 1, but polymerization was carried out at a temperature of 15° C. After a polymerization time of 170 minutes 26.7 g of isotactic polypropylene had been obtained. The activity was 2,880 kg of PP/mol of Zr.h. at an Mn of 54,000. Determination of APP gave a content of 0.7%. The $M_w/M_n$ value was 2.0.

EXAMPLE 3

The procedure was as in Example 1. The polymerization temperature was 0° C.; the polymerization time was 255 minutes. After this time 12.5 g of isotactic polypropylene had been obtained. The activity was 880 kg of PP/mol of Zr.h. at an Mn of 134,000. The $M_w/M_n$ value was 2.6. APP determination gave 0.2%.

EXAMPLE 4

The procedure was as in Example 1, but polymerization was carried out at a temperature of −10° C. 4.5 g of isotactic polypropylene had been obtained after a polymerization time of 270 minutes. The activity was 300 kg of PP/mol of Zr.h.; the Mn was 280,000. GPC determination gave an $M_w$ of 305,000 and an $M_n$ of 116,000, corresponding to an $M_w/M_n$ value of 2.6. Determination of APP gave a soluble fraction of 0.25%.

EXAMPLE 5

The procedure was as in Example 1, but polymerization was carried out at 40° C. After 150 minutes 34.8 g of polymer had been obtained, of which a low-molecular wax fraction of 7.5 g was soluble in toluene. The activity was 4,150 kg/mol of Zr.h. at an Mn of 12,000. GPC determination gave an $M_w/M_n$ value of 1.6 for the fraction insoluble in toluene.

EXAMPLE 6

The procedure was as in Example 1, but 70 ml of 1-butene were condensed in instead of propylene, and polymerization was carried out at −10° C. After 330 minutes the polymerization was discontinued, the product was washed with HCl solution and the solvent was removed. The polybutene formed dissolved in toluene at temperatures about 30° C. The yield was 9.1 g, which gives an activity of 500 kg of PB/mol of Zr.h.

EXAMPLE 7

The procedure was as in Example 1, with the modification that only 210 mg of methyl aluminoxane and $10^{-6}$ mol of zirconium compound were employed. 70 ml of propylene were then condensed in, and ethylene was injected up to an excess pressure of 0.3 bar. The polymerization time was 60 minutes at 25° C. Working up was carried out as in Example 5. 32.2 g of a copolymer containing ethylene and propylene units was obtained, the propylene sequences being linked in an isotactic manner.

EXAMPLE 8

The procedure was as in Example 7, with the modification that the amount of zirconium was $8.3 \times 10^{-7}$ mol and 15 ml of propylene were condensed in and ethylene was injected up to an excess pressure of 5.5 bar. The polymerization time was 10 minutes at 30° C. Working up was carried out as in Example 5. 9.4 g of a copolymer containing ethylene and propylene units were obtained.

EXAMPLE 9 AND COMPARISON EXAMPLE A 750 ml of anhydrous petroleum ether (boiling range 100°–120° C.) were placed in a 1,000 ml laboratory autoclave. The solvent was dried with a 10 Angström molecular sieve and was then flushed with dry argon. The solvent was heated to the process temperature under a pressure of 6 bar of dry nitrogen. In the course of this the nitrogen was replaced three times.

500 mg of methyl aluminoxane (MAO) were added in a countercurrent of inert gas, so that the activator concentration was $1.1 \times 10^{-2}$ mol/liter. The solution of the Ti or Zr compound was then added to the solution. The concentration of catalyst in the reactor was then as shown in Table 2. 8 bar of ethylene were injected with stirring (750 r.p.m.) in the course of 5 minutes. The amounts of polyethylene indicated had been obtained after a polymerization time of 2 hours. The results are collated in the Comparison Table 2.

We claim:

1. A process for the preparation of polyolefins by polymerizing olefins of the formula $CH_2=CHR$ in which $R = C_1-C_{10}$-alkyl, on their own or as a mixture, in solvents, liquid monomers or in the gas phase at a temperature from −50° to 200° C. by means of a soluble transition metal compound and aluminoxanes, which comprises carrying out the polymerization in the presence of a catalyst system which consists essentially of:
(a) ethylene-bis-(4,5,6,7-tetrahydroindenyl)-zirconium dichloride, and
(b) a methyl aluminoxane of the formula $Al_2O(CH_3)_4(Al(CH_3)O)_n$, for a linear methyl aluminoxane, or $(Al(CH_3)O)_{n+2}$ for a cyclic methyl aluminoxane, or combinations thereof, wherein n is a number from 4 to 20.

2. The process as claimed in claim 1 wherein said olefin or olefins of the formula $CH_2=CHR$ are mixed with ethylene when polymerized.

COMPARISON TABLE 1

| Example No. | Polymer | Polymerization Temp. °C. | Time Min. | Yield g | Activity kg/mol. of Zr · h. | APP-determination % crystalline | % soluble | GPC $M_w/M_n$ | $M_n$ |
|---|---|---|---|---|---|---|---|---|---|
| 1 | PP | 20 | 120 | 31.3 | 4750 | 99.0 | 1.0 | 1.9 | 41000 |
| 2 | PP | 15 | 170 | 26.7 | 2880 | 99.3 | 0.7 | 2.0 | 54000 |
| 3 | PP | 0 | 255 | 12.5 | 880 | 99.8 | 0.2 | 2.4 | 134000 |
| 4 | PP | −10 | 270 | 4.5 | 300 | 99.75 | 0.25 | 2.6 | 280000 |
| 5 | PP | 40 | 150 | 27.3 | 4150 | | | 1.6 | 12000 |
| 6 | PB | −10 | 330 | 9.1 | 500 | | | | |
| 7 | PP/PE | 25 | 60 | 32.2 | 32300 | | | | |
| 8 | PP/PE | 30 | 10 | 9.4 | 67900 | | | | |

COMPARISON TABLE 2

| (Comparison) Example No. | Test No. | Catalyst | concentration employed [mol/liter] | MAO-concentration [mol/liter] | Polymerization Temp. [°C.] | Weight [g] | KZA [gPE/mmol · h · bar] |
|---|---|---|---|---|---|---|---|
| A | 1 | 1 | $2.6 \times 10^{-6}$ | $1.1 \times 10^{-2}$ | 50 | 4.8 | 116 |
| | 2 | 1 | $7.8 \times 10^{-6}$ | $1.1 \times 10^{-2}$ | 50 | 10.3 | 83 |
| | 3 | 1 | $2.6 \times 10^{-6}$ | $1.1 \times 10^{-2}$ | 60 | 2.0 | 48 |
| | 4 | 1 | $2.6 \times 10^{-6}$ | $1.1 \times 10^{-2}$ | 70 | 1.4 | 35 |
| | 5 | 1 | $1.6 \times 10^{-6}$ | $1.1 \times 10^{-2}$ | 85 | 0.3 | 133 |
| | 6 | 1 | $7.3 \times 10^{-6}$ | $1.1 \times 10^{-2}$ | 85 | 0.7 | 58 |
| | 7 | 1 | $4.0 \times 10^{-6}$ | $1.1 \times 10^{-2}$ | 85 | 1.7 | 27 |
| 9 | 8 | 2 | $1.4 \times 10^{-6}$ | $1.1 \times 10^{-2}$ | 50 | 2.2 | 980 |
| | 9 | 2 | $1.4 \times 10^{-6}$ | $1.1 \times 10^{-2}$ | 60 | 6.7 | 2990 |
| | 10 | 2 | $1.4 \times 10^{-6}$ | $1.1 \times 10^{-2}$ | 70 | 18.9 | 8438 |
| | 11 | 2 | $1.4 \times 10^{-6}$ | $1.1 \times 10^{-2}$ | 80 | 44.6 | 19900 |
| | 12 | 2 | $1.5 \times 10^{-6}$ | $1.1 \times 10^{-2}$ | 85 | 83.5 | 34790 |

1 = Ethylene-bis-indenyltitanium dichloride
2 = Ethylene-bis-indenylzirconium dichloride
MAO = Methyl Aluminoxane

* * * * *